US006413502B1

(12) United States Patent
Bornstein et al.

(10) Patent No.: US 6,413,502 B1
(45) Date of Patent: *Jul. 2, 2002

(54) PREPARATION FOR DENTAL TREATMENT

(75) Inventors: Rolf Bornstein, Stockholm; Dan Ericson, Malmö, both of (SE)

(73) Assignee: Medi Team Dentalutveckling I Goteborg AB, Savedalen (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/308,163

(22) PCT Filed: Nov. 11, 1997

(86) PCT No.: PCT/SE97/01887

§ 371 (c)(1),
(2), (4) Date: Jul. 1, 1999

(87) PCT Pub. No.: WO98/20838

PCT Pub. Date: May 22, 1998

(30) Foreign Application Priority Data

Nov. 14, 1996 (SE) ................................ 9604210

(51) Int. Cl.⁷ ............................ A61K 7/20; A61K 7/22; C11D 3/395
(52) U.S. Cl. ................... 424/53; 433/215.1; 433/216.1; 424/54
(58) Field of Search ..................... 424/49–58

(56) References Cited

U.S. PATENT DOCUMENTS

| 3,903,252 A | * | 9/1975 | Stearns et al. ................. 424/49 |
| 3,998,945 A | | 12/1976 | Vit ............................... 424/53 |
| 4,271,030 A | * | 6/1981 | Brierley et al. ................ 252/98 |
| 4,561,994 A | * | 12/1985 | Rubin et al. ............ 252/187.23 |
| 4,710,217 A | | 12/1987 | Bailey et al. ................... 65/31 |
| 4,802,950 A | | 2/1989 | Croll ........................... 156/629 |
| 4,992,256 A | * | 2/1991 | Skaggs et al. ................. 424/49 |
| 5,688,756 A | * | 11/1997 | Garabedian et al. ........ 510/369 |
| 5,697,985 A | * | 12/1997 | Good et al. ..................... 8/528 |
| 5,827,810 A | * | 10/1998 | Brodbeck et al. ............ 510/369 |
| 5,851,421 A | * | 12/1998 | Choy et al. ............. 252/187.26 |
| 6,017,515 A | * | 1/2000 | Van Den Bosch ............. 424/53 |
| 6,100,728 A | * | 8/2000 | Argo et al. .................. 510/379 |

FOREIGN PATENT DOCUMENTS

| EP | 0 241 120 A2 | 10/1987 |
| EP | 0 398 893 B1 | 11/1990 |
| EP | 0 398 893 B1 | 10/1993 |
| WO | WO 89/05135 | 6/1989 |

* cited by examiner

Primary Examiner—Shep K. Rose
(74) Attorney, Agent, or Firm—Connolly Bove Lodge & Hutz

(57) ABSTRACT

The invention relates to a preparation for use in chemical-mechanical treatment of caries in the form of a two-component caries dissolving liquid in which one of the components consists of sodium hypochlorite and the other component of amino acids, preferably three amino-acids with different charge states; one neutral, one with a negative net charge and one with a positive net charge. A viscosity increasing substance in the form of 3% carboxy methyl cellulose, or any other polysaccharide, as well as a coloring agent, 0.04% Erythrosin, which is able to interact with carious tooth substance has been added to the amino acid component. This means that less liquid is spent, the liquid becomes easier to control and handle and the suspended material becomes more visible.

10 Claims, No Drawings

PREPARATION FOR DENTAL TREATMENT

CROSS REFERENCE TO RELATED APPLICATION

This application is the National Phase of international application No. PCT/SE97/01887, filed Nov. 11, 1997.

The present invention relates to a preparation for chemical-mechanical treatment of caries and to a method for producing the preparation.

In traditional caries treatment the attacked tooth substance is removed mechanically by means of a high-speed drill. Such a caries treatment is often a painful and unpleasant experience for the patient. Some of the patients feel so uncomfortable with the treatment that they wait far too long before they make a visit to a dentist, which means that it is often too late to save the caries attacked teeth. Extraction of the teeth is then the only treatment method that is left.

However, there are other methods which are based on a chemical-mechanical treatment for the removal of the caries attacked tooth substance. A method of this type is described in SE 460258. According to this method a two-component liquid is mixed and then immediately applied on the caries site. Functioning in a biological way, the liquid makes the caries attacked substance soft without causing any damage to the tooth or the soft tissue. After 10–15 seconds the dentist can start removing the softened carious substance by scraping. The scraping operation continues until all carious substance has been removed. Then the cavity is filled with a suitable material.

According to the patent the two-component liquid consists of a sodium hypochlorite component and a nitrogen-containing component. The nitrogen-containing component consists of three nitrogen-containing compounds with different charge states; one neutral, one with a negative net charge and one with a positive net charge.

Unlike the conventional mechanical caries treatment this biological treatment method is usually not painful at all. Neither does it require any investments in expensive equipments.

According to the treatment method the admixed two-component liquid is applied in drops on the tooth so that the entire carious site is covered and the caries affected tissue is softened. After 10–15 seconds a mechanical removal of the softened carious material can be initiated. The softened carious dentine (the tooth substance) is removed with the use of a scraping instrument. After some scraping the solution becomes turbid due to suspended carious substance and can be exhausted by suction or wiped away.

The above steps are repeated until the solution remains clear. In order to minimize any discomfort and the experience of pain for the patient the removal of the solution by means of a cold air stream or cold water flushing should be avoided. Instead, cotton pellets are used to remove the solution. When the carious substance has been completely removed the cavity is sealed with a suitable filling material.

For most carious lesions the treatment has to be repeated in several steps until the solution remains clear. Due to the repetition of the procedure a relatively large volume of the two-component liquid is required. Since the liquid has a low viscosity as well it easily spreads itself outside the carious site and there is a risk for liquid waste.

It might be difficult and/or time-consuming for the dentist to remove such a solution which has been spread or which has been unintentionally spilt outside the carious site.

An object of this invention is to provide a preparation for dental treatment where smaller volumes of the two-component liquid are required for the caries treatment.

Another object of the invention is to provide a preparation for dental treatment which facilitates the handling of the preparation during its application on the carious site.

According to the invention this is achieved through the addition to the caries dissolving two-component liquid of a viscosity increasing substance (gel substance) and a coloring agent which is able to interact with carious tooth substance.

According to a preferred embodiment the gel substance consists of methyl cellulose or any other polysaccharide and the coloring agent consists of Erythrosin (E 127 B).

According to the invention the preparation is produced with the addition of the viscosity increasing substance (gel substance) and the coloring agent to the amino acid containing component before this component is mixed with the sodium hypochlorite component, which takes place as near the treatment site as possible.

The advantage with the preparation according to this invention is that much smaller volumes of the preparation are required for the treatment. This means that the concentrations of the included active components can be increased, in turn resulting in a faster softening of the carious substance.

Through the increased viscosity a better control of where the solution is located is obtained. The risk for spillage is reduced. At the same time the suspended carious material becomes more visible since the suspended particles do not sink to the bottom of the solution so rapidly due to its higher viscosity.

The coloring agent makes the preparation more visible and this effect has been pronounced with the use of a certain coloring agent which has the ability to interact with carious tooth substance as well.

In the following an example of a suitable preparation will be described more in detail.

According to the invention the preparation consists of a sodium hypochlorite component, which has a strong dissolving effect on the carious substance, and a component with three amino acids, which, when mixed with the sodium hypochlorite component, become N-chlorinated and give compounds containing active chlorine which, while retaining a caries-dissolving quality, does not show the aggressiveness of sodium hypochlorite towards mucous membranes. The sodium hypochlorite and amino acid components as such could be of the type described in the above-mentioned SE 460 258 patent publication and therefore will not be described in any detail here.

Unlike the preparation described in the above-mentioned Swedish patent publication, the preparation in this case also includes an additional component in the form of a viscosity increasing material, such as gelatine or other gel substance, as well as a coloring agent. The gel substance consists of a 3% carboxymethylcellulose and the coloring agent of 0.04% Erythrosin (E 127 B) both of which are added to the amino acid component before this component is mixed with the sodium hypochlorite component. The concentrations therefore refer to un-mixed components. Gelatine and carboxymethylcellulose, like the amino acid component, have the advantage of reducing the aggressive influence of said sodium hypochlorite on mucous membranes.

The introduction of the gel substance has the additional advantage that smaller volumes of the preparation are required for the caries treatment. With the previous two-component solution typically 20 ml liquid was required when using a flow feeding system known as Caridex, while only 0.2 ml of the new solution with the additional gel substance was required for the treatment, which is 100 times smaller volume of the preparation. This gives the possibility to increase the concentrations of the active components.

By increasing the viscosity it becomes easier to control and handle the solution. The risk for spillage on other near-by tissue surfaces is reduced. By making the preparation viscous the suspended material becomes more visible during the treatment compared to treatment with the previous preparation. When so much of the carious material has been removed with the scraping instrument that no more turbidity appears, this is the first indication of a finished excavation. Making the slurry more visible, therefore facilitates the dental treatment.

Many preparations used in the dental technical field comprise different types of thickening agents, for instance etchant gel compositions which contain 37% phosphoric acid and which are made in gel form with different colors depending on the manufacturer. However, such etchant gels have no blurring effect like the carboxymethylcellulose composition used in the present application.

With the addition of a coloring agent the liquid becomes more visible, for instance in case of spillage. By using a coloring agent of a type which can interact with carious tooth substance, the suspended material is made more visible. According to the invention a coloring agent such as Erythrosin colors carious dentine to a certain extent and has therefore the advantage of making the carious dentine material more visible.

It is true that coloring agents are used in many technical preparations as such in the dental field. However, in such preparations the coloring agent is not specifically made to interact with carious dentine material as in our case and which substance is then removed with a scraping instrument according to the chemical-mechanical method of treatment.

What is claimed is:

1. A preparation for chemical-mechanical treatment of caries in the form of a two-component caries-dissolving liquid wherein said liquid consists of:
   a first component comprising sodium hypochlorite, wherein said first component is substantially free of viscosity increasing substances; and
   a second component comprising a viscosity increasing substance, a coloring agent adherent to suspended carious tooth substance, and amino acids; said viscosity increasing substance together with the amino acids having the ability to reduce the aggressive influence of the sodium hypochlorite on mucous membranes; and wherein said first and second components are arranged to be mixed by the dentist before the liquid is applied on the carious site to soften the caries effected tissue.

2. A preparation according to claim 1 wherein said the viscosity increasing substance is a gel substance or gelatine.

3. A preparation according to claim 2 wherein said the viscosity increasing substance is a carboxy methyle cellulose or other poly sacharide substance.

4. A preparation according to claim 1 wherein said the coloring agent is Erythrosin (E 127 B).

5. Method for the production of a preparation according to claim 1 wherein the two components are delivered as solutions and mixed as near as possible ahead of the dental treatment site wherein said the viscosity increasing substance and the coloring agent are brought together with the amino acid component before the mixing.

6. Method according to claim 5 wherein said the viscosity increasing substance and the coloring agent are delivered in the form of 3% carboxy metyle cellulose and 0.04% Erythrosin (E 127 B), respectively.

7. Method for the production of a preparation according to claim 2 wherein the two components are delivered as solutions and mixed as near as possible ahead of the dental treatment site wherein said the viscosity increasing substance and the coloring agent are brought together with the amino acid component before the mixing.

8. Method for the production of a preparation according to claim 3 wherein the two components are delivered as solutions and mixed as near as possible ahead of the dental treatment site wherein said the viscosity increasing substance and the coloring agent are brought together with the amino acid component before the mixing.

9. Method for the production of a preparation according to claim 4 wherein the two components are delivered as solutions and mixed as near as possible ahead of the dental treatment site wherein said the viscosity increasing substance and the coloring agent are brought together with the amino acid component before the mixing.

10. The preparation of claim 1 wherein said amino acids comprise three amino acids with different charge states; one neutral, one with a negative net charge and one with a positive net charge.

* * * * *